United States Patent
Miyazaki et al.

(10) Patent No.: US 12,352,766 B2
(45) Date of Patent: *Jul. 8, 2025

(54) IMMUNOASSAY METHOD FOR FREE AIM IN BIOLOGICAL SAMPLE, AND METHOD FOR DETECTING NASH IN SUBJECT

(71) Applicants: SEKISUI MEDICAL CO., LTD., Tokyo (JP); Toru Miyazaki, Tokyo (JP); SOCIAL WELFARE ORGANIZATION "SAISEIKAI" IMPERIAL GIFT FOUNDATION INC., Tokyo (JP)

(72) Inventors: Toru Miyazaki, Tokyo (JP); Takeshi Okanoue, Suita (JP); Tomohide Asai, Tokyo (JP); Yuka Kanetsuki, Tokyo (JP); Jiro Hirota, Tokyo (JP)

(73) Assignees: SEKISUI MEDICAL CO., LTD., Tokyo (JP); Toru Miyazaki, Tokyo (JP); SOCIAL WELFARE ORGANIZATION "SAISEIKAI" IMPERIAL GIFT FOUNDATION INC., Tokyo (JP)

( * ) Notice: Subject to any disclaimer, the term of this patent is extended or adjusted under 35 U.S.C. 154(b) by 996 days.

This patent is subject to a terminal disclaimer.

(21) Appl. No.: 17/427,294

(22) PCT Filed: Jan. 30, 2020

(86) PCT No.: PCT/JP2020/003416
§ 371 (c)(1),
(2) Date: Jul. 30, 2021

(87) PCT Pub. No.: WO2020/158858
PCT Pub. Date: Aug. 6, 2020

(65) Prior Publication Data
US 2022/0120762 A1    Apr. 21, 2022

(30) Foreign Application Priority Data

Jan. 31, 2019  (JP) ................................. 2019-015224

(51) Int. Cl.
| | |
|---|---|
| *G01N 33/68* | (2006.01) |
| *C07K 16/28* | (2006.01) |
| *G01N 33/53* | (2006.01) |
| *G01N 33/576* | (2006.01) |

(52) U.S. Cl.
CPC ..... *G01N 33/6893* (2013.01); *C07K 16/2896* (2013.01); *G01N 33/5306* (2013.01); *G01N 33/576* (2013.01); *G01N 2800/085* (2013.01)

(58) Field of Classification Search
CPC .......... G01N 33/6893; G01N 33/5306; G01N 33/576; G01N 2800/085; G01N 2333/4704; C07K 16/2896
See application file for complete search history.

(56) References Cited

U.S. PATENT DOCUMENTS

| 2015/0094268 A1 | 4/2015 | Miyazaki |
| 2018/0224437 A1 | 8/2018 | Miyazaki |
| 2019/0317096 A1* | 10/2019 | Miyazaki ......... G01N 33/57438 |

FOREIGN PATENT DOCUMENTS

| EP | 2 870 970 A1 | 5/2015 |
| WO | WO 2013/162021 A1 | 10/2013 |
| WO | WO 2017/022315 A1 | 2/2017 |
| WO | WO 2017/043617 A1 | 3/2017 |

OTHER PUBLICATIONS

Arai S, Kitada K, Yamazaki T, Takai R, Zhang X, Tsugawa Y, et al. "Apoptosis inhibitor of macrophage protein enhances intraluminal debris clearance and ameliorates acute kidney injury in mice." Nat. Med. 2016; 22: 183-193 (Year: 2016).*
Oshima M, Iwata Y, Furuichi K, Sakai N, Shimizu M, Hara A, et al. "Association of apoptosis inhibitor of macrophage (AIM) expression with urinary protein and kidney dysfunction." Clin Exp Nephrol. 2017; 21: 35-42 (Year: 2017).*
International Preliminary Report on Patentability and English translation of the Written Opinion of the International Searching Authority for International Application No. PCT/JP2020/003416, dated Aug. 12, 2021.
Extended European Search Report for European Application No. 20749087.1, dated Oct. 10, 2022.
Okanoue et al., "Serum levels of immunoglobulin M-free inhibitors of macrophage/CD5L as a predictive and early diagnostic marker for nonalcoholic steatohepatitis-associated hepatocellular carcinoma," Hepatology Research, 2022, pp. 1-11.
Chinese Office Action and Search Report for Chinese Application No. 202080011502.8, dated Mar. 8, 2024, with English translation.
European Office Action for European Application No. 20 749 087.1, dated Jun. 26, 2023.
Arai et al., "Apoptosis inhibitor of macrophage protein enhances intraluminal debris clearance and ameliorates acute kidney injury in mice", Nature Medicine, Jan. 4, 2016, vol. 22, No. 2, p. 183-193.
Arai et al., "Obesity-Associated Autoantibody Production Requires AIM to Retain the Immunoglobulin M Immune Complex on Follicular Dendritic Cells", Cell Reports, 2013, vol. 3, No. 4, p. 1187-1198.
CircuLex Human AIM/CD5L/Spα ELISA Kit User's Manual, MBL, 2014, total 17 pages.

(Continued)

*Primary Examiner* — Lyle Alexander
*Assistant Examiner* — Alison Claire Gerhard
(74) *Attorney, Agent, or Firm* — Birch, Stewart, Kolasch & Birch, LLP

(57) ABSTRACT

A problem to be solved is to further improve the specificity for free AIM of an antibody specifically reacting with free AIM and to diagnose NASH without imposing a burden on patients and medical staffs. The problem can be solved by an immunoassay method for free AIM in a biological sample containing complex AIM and free AIM, and the method comprises bringing the biological sample into contact with an antibody specifically reacting with free AIM in a presence of an anti-IgM antibody.

8 Claims, 4 Drawing Sheets

Specification includes a Sequence Listing.

(56) References Cited

OTHER PUBLICATIONS

International Search Report, issued in PCT/JP2020/003416, PCT/ISA/210, dated Mar. 31, 2020.
Koyama et al., "Activation of apoptosis inhibitor of macrophage is a sensitive diagnostic marker for NASH-associated hepatocellular carcinoma", Journal Gastroenterology, Oct. 30, 2017, vol. 53, pp. 770-779.
Miyazaki et al., "AIM associated with the IgM pentamer: attackers on stand-by at aircraft carrier", Cellular and Molecular Immunology, Jan. 29, 2018, vol. 15, p. 563-574.
Written Opinion of the International Searching Authority, issued in PCT/JP2020/003416, PCT/ISA/237, dated Mar. 31, 2020.

* cited by examiner

FIG.1

| ADDED ANTI-IgM ANTIBODY | SAMPLE | COUNT (-blank) | COUNT RATIO (STANDARD: NORMAL) | COUNT INCREASE/DECREASE RATIO |
|---|---|---|---|---|
| STANDARD (WITHOUT ANTI-IgM ANTIBODY) | F6+F7 | 567.4 | 100% | 0% |
|  | F14+F15 | 15636.7 | 100% | 0% |
| HBR-1 | F6+F7 | 535.0 | 94.3% | -5.7% |
|  | F14+F15 | 15664.1 | 100.2% | 0.2% |
| HBR-3 | F6+F7 | 501.1 | 88.3% | -11.7% |
|  | F14+F15 | 15298.9 | 97.8% | -2.2% |
| HBR-6 | F6+F7 | 497.1 | 87.6% | -12.4% |
|  | F14+F15 | 15337.8 | 98.1% | -1.9% |
| HBR-9 | F6+F7 | 523.5 | 92.3% | -7.7% |
|  | F14+F15 | 15572.5 | 99.6% | -0.4% |
| HBR-20 | F6+F7 | 464.1 | 81.8% | -18.2% |
|  | F14+F15 | 15575.7 | 99.6% | -0.4% |
| HBR-21 | F6+F7 | 517.5 | 91.2% | -8.8% |
|  | F14+F15 | 15266.3 | 97.6% | -2.4% |
| HBR-23 | F6+F7 | 517.8 | 91.3% | -8.7% |
|  | F14+F15 | 16170.8 | 103.4% | 3.4% |
| HBR-26 | F6+F7 | 516.3 | 91.0% | -9.0% |
|  | F14+F15 | 15686.0 | 100.3% | 0.3% |

| SOLID PHASE ANTIBODY: ANTIBODY NO.2 RUTHENIUM-LABELED ANTIBODY: ANTIBODY NO. 1 | WITH ADDITION OF ANTI-HUMAN IgM ANTIBODY | WITHOUT ADDITION OF ANTI-HUMAN IgM ANTIBODY |
|---|---|---|
| IgM-AIM / Total AIM | 2.4% | 7.5% |
| Free-AIM / Total AIM | 97.6% | 92.5% |

|  | MEASUREMENT SYSTEM OF PRESENT INVENTION | EXISTING MEASUREMENT SYSTEM |
|---|---|---|
| IgM-AIM / Total AIM | 2.5% | 19.7% |
| Free-AIM / Total AIM | 97.5% | 80.3% |

SEQUENCE LISTING

```
<160> NUMBER OF SEQ ID NOS: 4

<210> SEQ ID NO 1
<211> LENGTH: 347
<212> TYPE: PRT
<213> ORGANISM: human

<400> SEQUENCE: 1

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
                20                  25                  30

Cys Glu Gly Arg Val Glu Val Glu Gln Lys Gly Gln Trp Gly Thr Val
            35                  40                  45

Cys Asp Asp Gly Trp Asp Ile Lys Asp Val Ala Val Leu Cys Arg Glu
        50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu
        115                 120                 125

Ser Ser Phe Ser Pro Val Pro Glu Gly Val Arg Leu Ala Asp Gly Pro
    130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255
```

```
Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
                275                 280                 285

Lys Ser Leu Ser Pro Ser Phe Arg Asp Arg Lys Cys Tyr Gly Pro Gly
290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Gly
            340                 345

<210> SEQ ID NO 2
<211> LENGTH: 102
<212> TYPE: PRT
<213> ORGANISM: human

<400> SEQUENCE: 2

Val Arg Leu Val Gly Gly Leu His Arg Cys Glu Gly Arg Val Glu Val
1               5                   10                  15

Glu Gln Lys Gly Gln Trp Gly Thr Val Cys Asp Asp Gly Trp Asp Ile
            20                  25                  30

Lys Asp Val Ala Val Leu Cys Arg Glu Leu Gly Cys Gly Ala Ala Ser
        35                  40                  45

Gly Thr Pro Ser Gly Ile Leu Tyr Glu Pro Pro Ala Glu Lys Glu Gln
    50                  55                  60

Lys Val Leu Ile Gln Ser Val Ser Cys Thr Gly Thr Glu Asp Thr Leu
65                  70                  75                  80

Ala Gln Cys Glu Gln Glu Val Tyr Asp Cys Ser His Asp Glu Asp
                85                  90                  95

Ala Gly Ala Ser Cys Glu
            100

<210> SEQ ID NO 3
<211> LENGTH: 102
<212> TYPE: PRT
<213> ORGANISM: human

<400> SEQUENCE: 3

Val Arg Leu Ala Asp Gly Pro Gly His Cys Lys Gly Arg Val Glu Val
1               5                   10                  15

Lys His Gln Asn Gln Trp Tyr Thr Val Cys Gln Thr Gly Trp Ser Leu
            20                  25                  30

Arg Ala Ala Lys Val Val Cys Arg Gln Leu Gly Cys Gly Arg Ala Val
        35                  40                  45

Leu Thr Gln Lys Arg Cys Asn Lys His Ala Tyr Gly Arg Lys Pro Ile
    50                  55                  60

Trp Leu Ser Gln Met Ser Cys Ser Gly Arg Glu Ala Thr Leu Gln Asp
65                  70                  75                  80

Cys Pro Ser Gly Pro Trp Gly Lys Asn Thr Cys Asn His Asp Glu Asp
                85                  90                  95

Thr Trp Val Glu Cys Glu
            100

<210> SEQ ID NO 4
```

```
<211> LENGTH: 103
<212> TYPE: PRT
<213> ORGANISM: human

<400> SEQUENCE: 4

Leu Arg Leu Val Gly Gly Asp Asn Leu Cys Ser Gly Arg Leu Glu Val
1               5                   10                  15

Leu His Lys Gly Val Trp Gly Ser Val Cys Asp Asp Asn Trp Gly Glu
            20                  25                  30

Lys Glu Asp Gln Val Val Cys Lys Gln Leu Gly Cys Gly Lys Ser Leu
            35                  40                  45

Ser Pro Ser Phe Arg Asp Arg Lys Cys Tyr Gly Pro Gly Val Gly Arg
        50                  55                  60

Ile Trp Leu Asp Asn Val Arg Cys Ser Gly Glu Glu Gln Ser Leu Glu
65                  70                  75                  80

Gln Cys Gln His Arg Phe Trp Gly Phe His Asp Cys Thr His Gln Glu
                85                  90                  95

Asp Val Ala Val Ile Cys Ser
            100
```

IMMUNOASSAY METHOD FOR FREE AIM IN BIOLOGICAL SAMPLE, AND METHOD FOR DETECTING NASH IN SUBJECT

TECHNICAL FIELD

The present invention relates to an immunoassay method for free AIM in a biological sample, and an assay kit. The present invention also relates to a method for suppressing a non-specific reaction in an immunoassay method for free AIM in a biological sample. The present invention also relates to a method for detecting NASH in a subject and a diagnostic kit.

BACKGROUND ART

AIM (apoptosis inhibitor of macrophage) is a secretory blood protein with a molecular weight of about 50 kDa produced by tissue macrophages. AIM has a structure in which three scavenger recipient cysteine-rich (SRCR) domains having specific sequences containing many cysteine residues are connected in tandem, and the cysteine residues are considered to be disulfide-bonded to each other in each domain to form a compact spherical three-dimensional structure.

AIM is known to have the characteristic of binding to various molecules such as lipopolysaccharide, IgM, complement regulatory factors, and fatty acid synthetases. Particularly, AIM is known to exist in the form of a complex with IgM in the blood. Since IgM is a huge protein complex exceeding 500 kDa, AIM does not pass through the glomerulus and transfer to urine as long as AIM is bound to IgM, and a high blood concentration of AIM is maintained. When dissociated from IgM, AIM is promptly excreted into urine. Therefore, most of AIM forms a complex with IgM in the blood and are rarely present in the blood in a free state rather than as a conjugate.

In recent years, it has been clarified that AIM is involved in the progression of pathological conditions in various diseases such as insulin resistance or arteriosclerosis. For example, a relationship between free AIM present in a free form not bound to another binding partner and liver disease has been reported (Patent Document 1).

Among liver diseases, the number of patients with non-alcoholic fatty liver disease (NAFLD) is increasing in recent years, and it is estimated that about 15 to 20 million people in Japan are affected by NAFLD. Nonalcoholic fatty liver disease (NAFLD) is a general term for a pathological condition of non-drinkers developing fatty liver. NAFLD is classified into nonalcoholic steatohepatitis (NASH), which is also pathogenesis of liver cirrhosis and liver cancer, and nonalcoholic fatty liver (NAFL) with the pathological condition hardly progressing. In Japan, it is estimated that about 1.5 to 3 million people are affected by NASH.

CITATION LIST

Patent Literature

Patent Document 1: WO 2017/043617

SUMMARY OF INVENTION

Technical Problem

When a specific disease is diagnosed based on a measurement result of a free AIM amount, it is necessary to eliminate an amount of AIM forming a complex and measure only the free AIM amount. However, when free AIM is detected, complex AIM bound to another binding partner may also be detected. Therefore, a demand exists for a technique capable of eliminating an amount of AIM forming a complex and measuring only the free AIM amount without complicated operations.

Additionally, a biopsy of liver tissue is indispensable for a definitive diagnosis of NASH, and the biopsy of liver tissue is used for comprehending an amount of fat, a degree of inflammation, and a degree of progression of fibrosis to enable diagnosis of NASH. However, the biopsy of liver tissue involves piercing the liver with a needle to collect a portion of tissue or cells, which imposes an excessive burden on patients and medical staffs, and is associated with a risk of complications etc. Therefore, a demand exists for development of a new NASH diagnostic method that can be performed more easily and does not impose a burden on patients and medical staffs.

An object of the present invention is to provide an immunoassay method for measuring an amount of free AIM in a biological sample containing complex AIM and free AIM with excellent specificity, and a method for detecting NASH in a subject with excellent specificity and sensitivity.

Solution to Problem

Means for Solving Problems

As a result of intensive studies for solving the problem, the present inventor found that the specificity for free AIM of an antibody specifically reacting with free AIM can further be improved by using an anti-IgM antibody and that NASH can be detected in a subject by combining a use of an anti-IgM antibody and a use of an antibody specifically reacting with free AIM, thereby completing the present invention.

In Example 3 of Patent Document 1, it is described that no difference was observed in the amount of free AIM in the sera of a healthy person, a subject suffering from NAFL, and a subject suffering from NASH. Nonetheless, when an analysis was performed in the presence of an anti-IgM antibody, a significant difference was confirmed in the amount of free AIM in the sera of a subject suffering from NAFL and a subject suffering from NASH. This is surprising.

Specifically, the present invention is as follows.

<1> An immunoassay method for free AIM in a biological sample containing complex AIM and free AIM, the method comprising: bringing the biological sample into contact with an antibody specifically reacting with free AIM in a presence of an anti-IgM antibody.

<2> The immunoassay method for free AIM in a biological sample according to <1>, wherein the biological sample is a body fluid sample.

<3> The immunoassay method for free AIM in a biological sample according to <1> or <2>, wherein the antibody specifically reacting with free AIM is a monoclonal antibody.

<4> An assay kit for free AIM in a biological sample containing complex AIM and free AIM, comprising: an anti-IgM antibody; and an antibody specifically reacting with free AIM.

<5> The assay kit for free AIM in a biological sample according to <4>, wherein the biological sample is a body fluid sample.

<6> The assay kit for free AIM in a biological sample according to <4> or <5>, wherein the antibody specifically reacting with free AIM is a monoclonal antibody.

<7> A method for suppressing a non-specific reaction in an immunoassay for free AIM in a biological sample containing complex AIM and free AIM, the method comprising: bringing the biological sample into contact with an antibody specifically reacting with free AIM in the presence of an anti-IgM antibody.

<8> The method for suppressing a non-specific reaction according to <7>, wherein the biological sample is a body fluid sample.

<9> The method for suppressing a non-specific reaction according to <7> or <8>, wherein the non-specific reaction is a non-specific reaction due to IgM in the biological sample.

<10> A method for detecting NASH, comprising:
bringing a biological sample into contact with an antibody specifically reacting with free AIM in the presence of an anti-IgM antibody;
measuring an amount of free AIM in the biological sample by detecting a signal; and
comparing the measured amount of free AIM with a reference value.

<11> The method for detecting NASH according to <10>, wherein the biological sample is a body fluid sample.

<12> The method for detecting NASH according to <10> or <11>, wherein the antibody specifically reacting with free AIM is a monoclonal antibody.

<13> The method for detecting NASH according to any one of <10> to <11>, wherein NAFL and NASH are discriminated from each other.

<14> A diagnostic kit for NASH comprising: an anti-IgM antibody; and an antibody specifically reacting with free AIM.

<15> The diagnostic kit for NASH according to <14>, wherein a free AIM concentration in a body fluid sample is measured.

<16> The diagnostic kit for NASH according to <14> or <15>, wherein the antibody specifically reacting with free AIM is a monoclonal antibody.

The present invention also includes the following embodiments.

<A1> An immunoassay method for free AIM in a biological sample containing complex AIM and free AIM, the method comprising: bringing the biological sample into contact with an antibody specifically reacting with free AIM in a presence of an anti-IgM antibody.

<A2> The immunoassay method for free AIM in a biological sample according to <A1>, wherein the anti-IgM antibody is one or more selected from the group consisting of HBR-1, HBR-3, HBR-6, HBR-9, HBR20, HBR21, HBR23, and HBR26.

<A3> The immunoassay method for free AIM in a biological sample according to <A1> or <A2>, wherein a concentration of the anti-IgM antibody is 1 to 1000 µg/mL.

<A4> The immunoassay method for free AIM in a biological sample according to any one of <A1> to <A3>, wherein the biological sample is blood, serum, plasma, or urine.

<B1> An assay kit for free AIM in a biological sample containing complex AIM and free AIM, comprising: an anti-IgM antibody; and an antibody specifically reacting with free AIM.

<B2> The assay kit for free AIM in a biological sample according to <B1>, wherein the anti-IgM antibody is one or more selected from the group consisting of HBR-1, HBR-3, HBR-6, HBR-9, HBR20, HBR21, HBR23, and HBR26.

<B3> The assay kit for free AIM in a biological sample according to <B1> or <B2>, wherein a concentration of the anti-IgM antibody is 1 to 1000 µg/mL.

<B4> The assay kit for free AIM in a biological sample according to any one of <B1> to <B3>, wherein the biological sample is blood, serum, plasma, or urine.

<C1> A method for suppressing a non-specific reaction in an immunoassay method of free AIM in a biological sample containing complex AIM and free AIM, the method comprising: bringing the biological sample into contact with an antibody specifically reacting with free AIM in the presence of an anti-IgM antibody.

<C2> The method for suppressing a non-specific reaction according to <C1>, wherein the anti-IgM antibody is one or more selected from the group consisting of HBR-1, HBR-3, HBR-6, HBR-9, HBR20, HBR21, HBR23, and HBR26.

<C3> The method for suppressing a non-specific reaction according to <C1> or <C2>, wherein a concentration of the anti-IgM antibody is 1 to 1000 µg/mL.

<C4> The method for suppressing a non-specific reaction according to any one of <C1> to <C3>, wherein the biological sample is blood, serum, plasma, or urine.

<D1> A method for detecting NASH, comprising:
bringing a biological sample into contact with an antibody specifically reacting with free AIM in a presence of an anti-IgM antibody; measuring an amount of free AIM in the biological sample by detecting a signal; and comparing the measured amount of free AIM with a reference value.

<D2> The method for detecting NASH according to <D1>, wherein the anti-IgM antibody is one or more selected from the group consisting of HBR-1, HBR-3, HBR-6, HBR-9, HBR20, HBR21, HBR23, and HBR26.

<D3> The method for detecting NASH according to <D1> or <D2>, wherein the concentration of the anti-IgM antibody is 1 to 1000 µg/mL.

<D4> The method for detecting NASH according to any one of <D1> to <D3>, wherein the biological sample is blood, serum, plasma, or urine.

<E1> A diagnostic kit for NASH comprising: an anti-IgM antibody; and an antibody specifically reacting with free AIM.

<E2> The diagnostic kit for NASH according to <E1>, wherein the anti-IgM antibody is one or more selected from the group consisting of HBR-1, HBR-3, HBR-6, HBR-9, HBR20, HBR21, HBR23, and HBR26.

<E3> The diagnostic kit for NASH according to <E1> or <E2>, wherein a concentration of the anti-IgM antibody is 1 to 1000 µg/mL.

<E4> The diagnostic kit for NASH according to any one of <E1> to <E3>, wherein the biological sample is blood, serum, plasma, or urine.

Advantageous Effects of Invention

According to the present invention, in a biological sample containing complex AIM and free AIM, the specificity for free AIM of an antibody specifically reacting with free AIM can further be improved. According to the present invention, NASH can be diagnosed without imposing a burden on patients and medical staffs.

BRIEF DESCRIPTION OF DRAWINGS

FIG. 1 is a diagram showing a non-specific reaction suppressing effect when various anti-human IgM antibodies are added to a measurement system.

DESCRIPTION OF EMBODIMENTS (Biological Sample)

Figure 2:
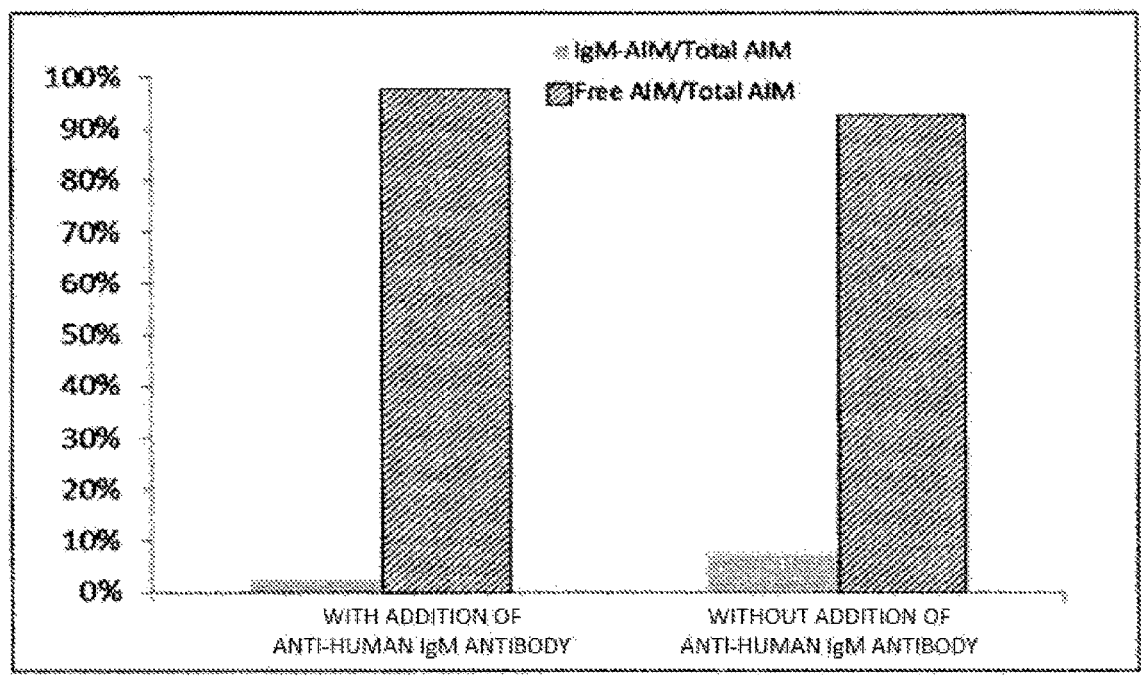
FIG. 2 is a diagram showing a non-specific reaction suppressing effect when an anti-human IgM antibody is added to a measurement system.

Examples of a biological sample analyzable in the present invention include solid tissues and body fluids derived from living bodies (organisms), and body fluids are preferably used. The biological sample analyzable in the present invention is more preferably a body fluid sample such as blood, serum, plasma, urine, saliva, sputum, tear fluid, otorrhea, or prostatic fluid, further preferably blood, serum, plasma, or urine. Examples of the living body or the subject include humans or animals (e.g., mice, guinea pigs, rats, monkeys, dogs, cats, hamsters, horses, bovines, and pigs), and are preferably humans. The biological sample from the subject may be collected or prepared at the time of implementation of the present invention or may preliminarily be collected or prepared and stored. The person preparing the sample and the person analyzing an amount of free AIM in the sample may be different. The biological sample can be an in vivo sample. The biological sample can be collected from a subject possibly suffering from NASH or a subject suffering from NASH. In the present invention, the biological sample contains both free AIM and complex AIM.

(AIM)

AIM (apoptosis inhibitor of macrophage) is a secretory blood protein with a molecular weight of about 50 kDa produced by tissue macrophages. AIM has a structure in which three scavenger recipient cysteine-rich (SRCR) domains, i.e., specific sequences containing many cysteine residues, are connected in tandem, and the cysteine residues are considered to be disulfide-bonded to each other in each domain to form a compact spherical three-dimensional structure.

Human AIM is composed of 347 amino acids represented by SEQ ID NO: 1 and contains three SRCR domains rich in cysteine. The SRCR1 domain corresponds to amino acid numbers 24 to 125 in the amino acid sequence represented by SEQ ID NO: 1. The SRCR2 domain corresponds to amino acid numbers 138 to 239 in the amino acid sequence represented by SEQ ID NO: 1. The SRCR3 domain corresponds to amino acid numbers 244 to 346 in the amino acid sequence represented by SEQ ID NO: 1.

The amino acid sequence of human AIM is as follows.

(SEQ ID NO: 1)
MALLFSLILAICTRPGFLASPSGVRLVGGLHRCEGRVEVEQKGQWGTVCD

DGWDIKDVAVLCRELGCGAASGTPSGILYEPPAEKEQKVLIQSVSCTGTE

DTLAQCEQEEVYDCSHDEDAGASCENPESSFSPVPEGVRLADGPGHCKGR

VEVKHQNQWYTVCQTGWSLRAAKVVCRQLGCGRAVLTQKRCNKHAYGRKP

IWLSQMSCSGREATLQDCPSGPWGKNTCNHDEDTWVECEDPFDLRLVGGD

NLCSGRLEVLHKGVWGSVCDDNWGEKEDQVVCKQLGCGKSLSPSFRDRKC

YGPGVGRIWLDNVRCSGEEQSLEQCQHRFWGFHDCTHQEDVAVICSG

Specifically, the amino acid sequences of the SRCR1 domain, the SRCR2 domain, and the SRCR3 domain in human AIM are as follows.

SRCR1 domain:
(SEQ ID NO: 2)
VRLVGGLHRCEGRVEVEQKGQWGTVCDDGWDIKDVAVLCRELGCGAASGT

PSGILYEPPAEKEQKVLIQSVSCTGTEDTLAQCEQEEVYDCSHDEDAGAS

CE

SRCR2 domain:
(SEQ ID NO: 3)
VRLADGPGHCKGRVEVKHQNQWYTVCQTGWSLRAAKVVCRQLGCGRAVLT

QKRCNKHAYGRKPIWLSQMSCSGREATLQDCPSGPWGKNTCNHDEDTWVE

CE

SRCR3 domain:
(SEQ ID NO: 4)
LRLVGGDNLCSGRLEVLHKGVWGSVCDDNWGEKEDQVVCKQLGCGKSLSP

SFRDRKCYGPGVGRIWLDNVRCSGEEQSLEQCQHRFWGFHDCTHQEDVAV

ICS (Free AIM)

In this description, the "free AIM" means AIM existing in a free state without being bound to other substances such as lipopolysaccharide or IgM. On the other hand, in this description, AIM bound to other substances such as lipopolysaccharide or IgM and existing in a state of a complex is referred to as complex AIM. The free AIM is preferably a human AIM existing in a free state. The free AIM is preferably human free AIM, and the complex AIM is preferably human complex AIM.

(Anti-IgM Antibody)

The term "anti-IgM antibody" as used herein means an antibody having a property of binding to IgM. In other words, the "anti-IgM antibody" means a substance from which human IgM and a precipitation line are generated by the Ouchterlony method. The antibody may have a binding property to another antigen as long as the antibody has a binding property to IgM and the effect of the present invention is not impaired. The anti-IgM antibody used in the present invention is preferably an anti-human IgM antibody. Although both a polyclonal antibody and a monoclonal antibody can be used as the anti-IgM antibody used in the present invention, a monoclonal antibody is preferably used from the viewpoint of ensuring the sensitivity of the antibody specifically reacting with free AIM. The anti-IgM antibody may be a functional fragment capable of binding to IgM. In the immunoassay method of the present invention, by using the anti-IgM antibody for a human serum sample, the non-specific reaction due to complex AIM can be reduced to 50% or less, preferably 40% or less, as compared to the case where the anti-IgM antibody is not added.

A commercially available anti-IgM antibody can also be used as the anti-IgM antibody used in the present invention. The commercially available anti-IgM antibody can be HBR-1, HBR-3, HBR-6, HBR-9, HBR20, HBR21, HBR23, HBR26 (SCANTIBODIES), etc. HBR-6 and/or HRB-20 is preferably used since non-specific reactions are effectively prevented.

The additive concentration of the anti-IgM antibody is not particularly limited as long as a sufficient non-specific reaction suppressing effect is achieved and a main reaction of immunoassay is not affected, and in the case of a monoclonal antibody, the antibody is desirably used in a concentration range of 1 to 1000 µg/mL, more desirably 10 to 1000 µg/mL, further desirably 10 to 300 µg/mL. In the case of a polyclonal antibody, the antibody is desirably used in a concentration range of 0.01 to 2 wt %, desirably used in a concentration range of 0.03 to 2 wt %, further desirably used in a concentration range of 0.05 to 1 wt %.

In the present invention, the binding affinity of the anti-IgM antibody to IgM is not particularly limited as long as the effect of the present invention can be obtained, and, for example, the binding affinity to IgM can be Kd of at least about $10^{-4}$ M, at least about $10^{-5}$ M, at least about $10^{-6}$ M, at least about $10^{-7}$ M, at least about $10^{-8}$ M, at least about $10^{-9}$ M, at least about $10^{-10}$ M, at least about $10^{-11}$ M, at least about $10^{-12}$ M or more.

The anti-IgM antibody can be prepared as either a monoclonal antibody or a polyclonal antibody according to a known method. The monoclonal antibody can be obtained by, for example, isolating spleen cells or lymph node cells, which are antibody-producing cells, from a non-human mammal immunized with IgM or IgM fragments, by fusing the cells with a myeloma-derived cell line having a high proliferative capacity to produce a hybridoma, and purifying an antibody produced by this hybridoma. The polyclonal antibody can be obtained from the serum of an animal immunized with IgM or IgM fragments. Examples of immunogens include, but not limited to, IgM or IgM fragments of primates such as humans and monkeys, rodents such as rats and mice, dogs, cats, horses, sheep, and pigs.

The anti-IgM antibody can be a whole antibody molecule as well as a fragment of an antibody having an antigen-antibody reaction activity and can be an antibody obtained through an immunization step of an animal as described above or obtained by using a gene recombination technique or can be a chimeric antibody. The fragment of the antibody is preferably a functional fragment; examples thereof include F(ab')2, Fab', scFv, etc.; and these fragments can be produced by processing the antibody obtained as described above with a proteolytic enzyme (e.g., pepsin or papain), or by cloning of DNA of the antibody and expression in a culture system using *Escherichia coli* or yeast.

In this description, "non-specific reaction" means that a substance other than free AIM binds to the anti-AIM antibody used in the present invention. In the present invention, a non-specific reaction due to complex AIM, or particularly, complex AIM having IgM bound as a binding partner can be suppressed by using the anti-IgM antibody.

(Antibody Specifically Reacting with Free AIM)

In this description, the "antibody specifically reacting with free AIM" means an antibody reacting only with free AIM and not substantially reacting with complex AIM in the absence of an anti-IgM antibody. In this description, "not substantially reacting with complex AIM" means that when a reactivity of an antibody is measured by a method known to those skilled in the art, the binding force to complex AIM is less than 10% when the binding force to free AIM is 100. In this description, the "anti-AIM antibody" means an antibody reacting with free AIM. Therefore, the term "anti-AIM antibody" as used herein includes an antibody specifically reacting with free AIM and an antibody reacting with both free AIM and complex AIM.

The antibody specifically reacting with free AIM used in an immunoassay method of the present invention can bind to an epitope in the SRCR2 domain of human AIM. The antibody specifically reacting with free AIM used in the immunoassay method of the present invention preferably binds to an epitope within the SRCR2 domain of human AIM and does not bind to the SRCR1 domain. The antibody specifically reacting with free AIM used in the immunoassay method of the present invention more preferably binds to an epitope in the SRCR2 domain of human AIM and does not bind to either the SRCR1 domain or the SRCR3 domain.

The immunoassay method of the present invention uses at least one antibody specifically reacting with free AIM. In the case of performing a so-called sandwich assay in which free AIM to be measured is sandwiched between two antibodies recognizing different epitopes, one of the antibodies may be an antibody specifically reacting with free AIM and the other antibody may be an anti-AIM antibody, or preferably, both of the two antibodies are antibodies specifically reacting with free AIM. In the case of performing a so-called sandwich assay in which free AIM to be measured is sandwiched between two antibodies recognizing different epitopes, the two antibodies preferably recognize different epitopes. In the case of performing an ECL method or ELISA method described later, an antibody specifically reacting with free AIM is preferably used as a solid phase antibody immobilized on a solid phase.

The binding affinity of the antibody specifically reacting with free AIM to free AIM used in the immunoassay method of the present invention is not particularly limited as long as the effect of the present invention can be obtained, and, for example, the binding affinity to IgM can be Kd of at least about $10^{-4}$ M, at least about $10^{-5}$ M, at least about $10^{-6}$ M, at least about $10^{-7}$ M, at least about $10^{-8}$ M, at least about $10^{-9}$ M, at least about $10^{-10}$ M, at least about $10^{-11}$ M, at least about $10^{-12}$ M or more.

Whether an antibody and a specific compound such as complex AIM "substantially do not react" can be confirmed by an antigen solid phase ELISA method, a competitive ELISA method, a sandwich ELISA method, etc. as well as by a method (SPR method) using the principle of surface plasmon resonance etc. The SPR method can be performed by using devices, sensors, and reagents commercially available under the name of Biacore (registered trademark).

In the immunoassay method of the present invention, the presence of the anti-IgM antibody in the reaction system can reduce the reactivity between the antibody specifically reacting with free AIM and complex AIM. Although the timing of adding the anti-IgM antibody to the measurement system is not particularly limited as long as the effects of the present invention can be obtained, the anti-IgM antibody is preferably added before or at the same time as the addition of the antibody specifically reacting with free AIM.

The antibody specifically reacting with free AIM can be prepared as either a monoclonal antibody or a polyclonal antibody according to a known method. The monoclonal antibody can be obtained by, for example, isolating spleen cells or lymph node cells, which are antibody-producing cells, from a non-human mammal immunized with free AIM or a free AIM fragment and/or complex AIM or a complex AIM fragment, fusing the cells with a myeloma-derived cell line having a high proliferative capacity to produce a hybridoma, and purifying an antibody produced by this hybridoma. The polyclonal antibody can be obtained from the serum of an animal immunized with free AIM or a free AIM fragment and/or complex AIM or a complex AIM fragment. Examples of immunogens include, but not limited to, free AIM or free AIM fragments and/or complex AIM or complex AIM fragments of primates such as humans and monkeys, rodents such as rats and mice, dogs, cats, horses, sheep, and pigs.

The antibody specifically reacting with free AIM can be a whole antibody molecule as well as a fragment of an antibody having an antigen-antibody reaction activity. The antibody can be an antibody obtained through an immunization step of an animal as described above or obtained by using a gene recombination technique or can be a chimeric antibody. The fragment of the antibody is preferably a functional fragment, and examples thereof include F(ab')$_2$, Fab', scFv, etc. These fragments can be produced by processing the antibody obtained as described above with a proteolytic enzyme (e.g., pepsin or papain), or by cloning of DNA of the antibody and expression in a culture system using *Escherichia coli* or yeast.

Although "reacting" with free AIM, "recognizing" free AIM, and "binding" to free AIM are synonymously used in this description, these must be construed in the broadest sense without being limited to these exemplifications. Whether an antibody "reacts" with an antigen (compound) such as free AIM can be confirmed by an antigen solid phase ELISA method, a competitive ELISA method, a sandwich ELISA method, etc. as well as by a method (SPR method) using the principle of surface plasmon resonance etc. The SPR method can be performed by using devices, sensors, and reagents commercially available under the name of Biacore (registered trademark).

In this description, an "insoluble carrier" may be represented as a "solid phase", and physically or chemically supporting an antigen or antibody with an insoluble carrier or the supporting state may be represented as "immobilizing", "immobilized", or "solid phased". The term "analysis", "detection", or "measurement" must be construed in the broadest sense, including the existence proof and/or the quantitation of free AIM and must not be construed in a limited manner in any sense.

(Immunoassay Method)

Examples of the immunoassay method of the present invention include, but not limited to, electrochemiluminescence immunoassay (ECL method), ELISA, enzyme immunoassay, an immunohistochemical staining method, a surface plasmon resonance method, latex agglutination immunoassay, chemiluminescence immunoassay, a fluorescent antibody method, radioimmunoassay, an immunoprecipitation method, a Western Blot method, immunochromatography, the EATA method (Electrokinetic Analyte Transport Assay), and high performance liquid chromatography (HPLC).

By using a labeled antibody (secondary antibody) that can bind to the antibody used, an amount of the antibody bound to free AIM can be measured, and an amount of free AIM in a biological sample can thereby be measured. Examples of a labeling substance for producing the labeled antibody include enzymes, fluorescent substances, chemical luminescent substances, biotin, avidin, radioisotopes, colloidal gold particles, or colored latex. Those skilled in the art can appropriately select the immunoassay method depending on an antibody and a labeling substance used.

The electrochemiluminescence immunoassay (ECL method) is preferably used as the immunoassay method. The electrochemiluminescence immunoassay (ECL method) means a method of calculating an amount of an analyte by causing a labeling substance to emit light by an electrochemical stimulus and detecting an amount of luminescence. In the electrochemiluminescence immunoassay (ECL method), a ruthenium complex can be used as a labeling substance. The amount of luminescence of this ruthenium complex can be detected by disposing an electrode on a solid phase (microplate or beads etc.) and causing an electrochemical stimulus on the electrode.

Although the antibody specifically reacting with free AIM may be used as either a solid phase antibody or a detection antibody, the electrochemiluminescence immunoassay (ECL method) is preferably performed by using the antibody specifically reacting with free AIM as a solid phase antibody and the anti-AIM antibody recognizing an epitope different from the solid phase antibody as a detection antibody (labeled antibody). When an antibody specifically reacting with free AIM is used as a solid phase antibody while an anti-AIM antibody is used as a labeled antibody, and beads and a ruthenium complex are used as a solid phase and a label, respectively, the measurement principle is as follows. The following describes the measurement principle in an embodiment of the present invention and does not limit the scope of the present invention at all.

1. When the beads having the antibody specifically reacting with free AIM bound thereto are reacted with a sample in the presence of the anti-IgM antibody, the free AIM in the sample binds to the solid phase antibody bound to the beads.

2. After washing the beads, a ruthenium-labeled antibody is reacted with the free AIM bound to the beads and is bound in a sandwich shape.

3. After washing the beads, when electrical energy is applied on the electrode, the ruthenium complex emits light depending on an amount of the ruthenium-labeled antibody bound to the beads via the free AIM. By measuring this amount of luminescence, the free AIM in the sample can be measured.

An antibody specifically reacting with free AIM and recognizing an epitope different from the solid phase antibody can also be used as the ruthenium-labeled antibody.

Among the immunoassays, the ELISA method using an enzyme label is also preferable since a target can easily and quickly be measured. In the case of sandwich ELISA, an insoluble carrier having an antibody specifically reacting with free AIM immobilized thereto and an anti-AIM antibody labeled with a labeling substance and recognizing an epitope different from the immobilized antibody can be used. In this case, the insoluble carrier is preferably a plate (immunoplate), and the labeling substance can appropriately be selected and used.

Although the antibody specifically reacting with free AIM may be used as either a solid phase antibody or a detection antibody, the sandwich ELISA is preferably performed by using the antibody specifically reacting with free AIM as a solid phase antibody and the anti-AIM antibody recognizing an epitope different from the solid phase antibody as a detection antibody (labeled antibody). The antibody specifically reacting with free AIM immobilized on the insoluble carrier captures the free AIM in the sample and forms an antibody-free AIM complex on the insoluble carrier in the presence of the anti-IgM antibody. The antibody labeled with the labeling substance binds to the captured free AIM to form a sandwich with the antibody-free AIM complex described above. The free AIM in the sample can be measured by measuring an amount of the labeling substance by a method corresponding to the labeling substance. For specific methods, such as a method for immobilizing the antibody on the insoluble carrier and a method for binding the antibody and the labeling substance, the methods well known to those skilled in the art can be used without limitation.

An antibody specifically reacting with free AIM and recognizing an epitope different from the solid phase antibody can also be used as the labeled antibody. The high performance liquid chromatography method (HPLC method) or the EATA method (Electrokinetic Analyte Transport Assay) can also be used as the immunoassay method.

The EATA method can be performed by using μTAS Wako i30 manufactured by FUJIFILM Wako Pure Chemical Corporation.

A latex immunoagglutination method (hereinafter also referred to as an LTIA method) is a typical particle agglutination immunoassay and is also preferable as the immunoassay method. In the LTIA method, latex particles carrying an antibody to a target component are used, and a degree of agglutination (turbidity) of the latex particles caused by binding between an antigen that is the target component and the antibody-supporting latex particles forming an antigen-antibody complex is detected by optical means (e.g., a turbidimetric method for measuring transmitted light, a turbidity method for measuring scattered light), so that the target component can be analyzed. In the immunoassay method of the present invention, latex particles carrying the antibody specifically reacting with free AIM are used, and a degree of agglutination of the latex particles caused by binding between free AIM that is the target component and the antibody-supporting latex particles forming an antigen-antibody complex can be detected by optical means. When the LTIA method is adopted, two or more antibodies specifically binding to free AIM can be used, or the antibody specifically reacting with free AIM and the antibody having a property of reacting with both free AIM and complex AIM can also be used.

[2] Assay Kit for Measuring Amount of Free AIM

An assay kit for a free AIM amount of the present invention includes an anti-IgM antibody and at least one antibody specifically reacting with free AIM. The assay kit of the present invention can also include other test reagents, specimen diluents, and/or instructions for use.

The assay kit for a free AIM amount of the present invention preferably includes (1) to (3) below:

(1) a solid phase on which an antibody specifically reacting with free AIM is immobilized;

(2) an anti-AIM antibody labeled with an electrochemical luminescent substance and recognizing an epitope different from the immobilized antibody; and (3) an anti-IgM antibody.

When the ECL method is used, the assay kit of the present invention preferably includes a solid phase on which an antibody specifically reacting with free AIM is immobilized, and an anti-AIM antibody labeled with an electrochemical luminescent material such as a ruthenium complex. For example, in the assay kit using microbeads as the solid phase, a biological sample is added to and reacted with the microbeads on which the antibody specifically reacting with free AIM is solid-phased in the presence of an anti-IgM antibody, and the sample is then removed and washed. Subsequently, an anti-AIM antibody labeled with an electrochemical luminescent material and recognizing an epitope different from the antibody specifically reacting with free AIM is added and reacted. After washing the microbeads, electric energy is applied for luminescence, and an amount of luminescence of the labeling substance can be measured to obtain a free AIM concentration.

At least one of the immobilized antibody and the labeled antibody may be the antibody specifically reacting with free AIM, and the antibody specifically reacting with free AIM and recognizing an epitope different from the solid phase antibody can also be used as the antibody labeled with an electrochemical luminescent substance.

When the sandwich ELISA method is used, the assay kit includes at least (1) to (3) below:

(1) an insoluble carrier on which an antibody (solid phase antibody) specifically reacting with free AIM is immobilized;

(2) an anti-AIM antibody (labeled antibody) labeled with a labeling substance and recognizing an epitope different from the solid phase antibody; and (3) an anti-IgM antibody.

In such an assay kit, first, a biological sample is added to the insoluble carrier on which the solid phase antibody is immobilized in the presence of the anti-IgM antibody, and is then incubated, and the sample is removed and washed. The labeled antibody is added and then incubated, and a substrate is added for coloring. The free AIM concentration in the biological sample can be obtained by measuring the coloring with a plate reader etc.

At least one of the immobilized antibody and the labeled antibody may be the antibody specifically reacting with free AIM, and the antibody specifically reacting with free AIM and recognizing an epitope different from the solid phase antibody can also be used as the labeled antibody.

When the LTIA method is used, the assay kit can be a free AIM assay kit using the LTIA method including at least (1) to (3) below:

(1) latex particles on which an antibody (first solid phase antibody) specifically reacting with free AIM is immobilized;

(2) latex particles on which an anti-AIM antibody (second solid phase antibody) recognizing an epitope different from the solid phase antibody is immobilized; and (3) an anti-IgM antibody.

In such an assay kit, the first solid phase antibody and the second solid phase antibody aggregate via free AIM in the presence of anti-IgM antibody. The free AIM concentration in the biological sample can be obtained by detecting a degree of agglutination by using optical means.

(NASH)

Nonalcoholic fatty liver disease (NAFLD) is roughly classified into simple fatty liver in which fat is only deposited in hepatocytes, and steatohepatitis in which fat deposition is accompanied by hepatocyte degeneration/necrosis and inflammation as well as fibrosis. "NASH" means the latter. Therefore, in this description, "NASH" means a nonalcoholic fatty liver disease (NAFLD) other than simple fatty liver in which fat is only deposited in hepatocytes.

The pathological diagnosis of NASH can be performed according to Evidence-based Clinical Practice Guidelines for Nonalcoholic Fatty Liver Disease/Nonalcoholic Steatohepatitis (2014 edition) of the Japanese Society of Gastroenterology, for example. Specifically, patients can be classified based on the Mattenoni classification described on page 80 of the guideline, and Types 3 and 4 can be diagnosed as NASH. Types 1 and 2 can be diagnosed with NAFL. Additionally, patients are classified based on NAS (NAFLD Activity Score) described on page 82 of the guideline, and a patient having NAS of 5 points or more is highly likely to have NASH. Based on the diagnostic criteria of Yoonossi described on page 82 of the guideline, NASH can be diagnosed when (1) or (2) below is satisfied.

(1) In addition to hepatocyte fatty change (regardless of degree), centrilobular ballooning of hepatocytes and a Mallory-Denk body are observed.

(2) In addition to hepatocyte fatty change, centrilobular pericellular/perisinusoidal fibrosis or bridging fibrosis is observed.

In this description, "NASH" includes liver cirrhosis with advanced NASH and does not include hepatocellular carcinoma with advanced NASH.

Patent Document 1 describes that no difference was found in the amount of free AIM in the sera of the subjects suffering from NAFL and the subjects suffering from NASH. Nevertheless, when the analysis was performed in the presence of an anti-IgM antibody, a significant difference could be confirmed in the amount of free AIM in the sera of the subjects suffering from NAFL and the subjects suffering from NASH. In Patent Document 1, it is presumed that a non-specific reaction due to complex AIM occurred in the immunoassay method for free AIM and prevented generation of a significant difference between the subjects.

After the detection or method of NAFLD or NASH of the present invention is performed, another NASH detection method may be performed on a patient and/or a NASH therapeutic agent may be administered to a patient, if necessary.

(Signal)

The signal is not particularly limited as long as the free AIM amount can accurately be measured, and any signal known to those skilled in the art can be adopted. The signal can be a signal emitted by the labeling substance for labeling the antibody. Examples of the labeling substance for labeling the antibody include enzymes, fluorescent substances, chemiluminescent substances, biotin, avidin, radioisotopes, colloidal gold particles, or colored latex. A method for binding the labeling substance and the antibody can be a method such as a glutaraldehyde method, a maleimide method, a pyridyl disulfide method, or a periodic acid method, which can be used by those skilled in the art. For any of the labeling substances and the binding methods, a known method can be used without being limited to the above. For example, when an enzyme such as peroxidase or alkaline phosphatase is used as the labeling substance, the enzyme activity can be measured by using the specific substrate of the enzyme (e.g., 1,2-phenylenediamine or 3,3',5,5'-tetramethylbenzidine when the enzyme is horseradish peroxidase, or p-nitrophenyl phosphate when the enzyme is alkaline phosphatase), and when biotin is used as the labeling substance, at least avidin labeled with a labeling substance other than biotin is typically reacted therewith.

When the LTIA method is used, a degree of latex agglutination can be optically measured by using scattered light intensity, transmitted light intensity, absorbance, etc., and the degree of latex agglutination can be used as the signal. The optical measurement can be performed by using any general biochemical automatic analyzer represented by an optical device capable of detecting scattered light intensity, transmitted light intensity, absorbance, etc., or an optical device equipped with a plurality of these detection methods. A conventionally known method is used as the method for optically measuring a degree of agglutination, and examples thereof include a turbidimetric method in which the formation of agglutination is perceived as an increase in turbidity, a method in which the formation of agglutination is perceived as a change in particle size distribution or average particle size, and an integrating sphere turbidity method in which a change in forward scattered light due to the formation of agglutination is measured by using an integrating sphere for comparison of the ratio to the transmitted light intensity.

(Reference Value)

The method for detecting NASH of the present invention includes comparing a measured free AIM amount with a reference value. In the method for detecting NASH of the present invention, NASH can be detected by using the fact that the amount of free AIM in the subject is higher than the amount of free AIM in a healthy subject group or an NAFL group. Specifically, for example, when the amount of free AIM in the subject is equal to or greater than a threshold value (reference value) for the healthy subject group or the NAFL group, it can be determined that a possibility of having NASH is high.

The range of numerical values can be used as the reference value. In the case of diagnosing whether a person has NASH, a range of amounts of free AIM in biological samples of subjects having been diagnosed as having NASH and subjects having been diagnosed as not having NASH is measured in advance, and if the amount of free AIM in the biological sample of a subject falls within the range of the amount of free AIM in the biological sample of healthy subjects or subjects having NAFL, this subject is highly likely not to have NASH, and if the amount falls within the range of the amount of free AIM in the biological sample of the subjects suffering from NASH, the subject is highly likely to have NASH.

The threshold value (reference value) is expected to change depending on various conditions such as underlying disease, gender, and age; however, those skilled in the art can appropriately select a proper population corresponding to a subject and can determine a normal value range or the threshold value by performing statistical processing on data obtained from the population. For example, the reference value can be a value in the human serum of 0.1 µg/mL, 0.2 µg/mL, 0.3 µg/mL, 0.4 µg/mL, 0.5 µg/mL, 0.6 µg/mL, 0.7 µg/mL, 0.8 µg/mL, 0.9 µg/mL, 1.0 µg/mL, 1.1 µg/mL, 1.2 µg/mL, 1.3 µg/mL, 1.4 µg/mL, 1.5 µg/mL, 1.6 µg/mL, 1.7 µg/mL, 1.8 µg/mL, 1.9 µg/mL, 2.0 µg/mL, 2.1 µg/mL, 2.2 µg/mL, 2.3 µg/mL, 2.4 µg/mL, 2.5 µg/mL, 2.6 µg/mL, 2.7 µg/mL, 2.8 µg/mL, 2.9 µg/mL, 3.0 µg/mL, 3.1 µg/mL, 3.2 µg/mL, 3.3 µg/mL, 3.4 µg/mL, or 3.5 µg/mL.

The method for detecting NASH of the present invention can also monitor a progress of NAFL to NASH in a subject. When an amount of free AIM in a subject suffering from NAFL is measured at a particular time point, and an amount of free AIM of this subject is measured again after a certain period (e.g., after 1, 3, 6, or 12 months, or 3 to 6 months), if the amount of free AIM exceeds the reference value, it can be determined that the progress from NAFL to NASH has occurred. On the contrary, if the amount is lower than the reference value, it can be determined that the progress from NAFL to NASH has not occurred.

(Diagnostic Kit for NASH)

The assay kit for a free AIM amount can be used as a diagnostic kit for NASH. Particularly, the assay kit for free AIM using the ECL method including (1) to (3), the assay kit for a free AIM amount using the sandwich ELISA method including (1) to (3), and the assay kit for a free AIM amount using the LTIA method including (1) to (3), can be used as the diagnostic kit for NASH.

The present invention will hereinafter specifically be described with examples; however, these examples do not limit the scope of the present invention. Unless otherwise described, "%" denotes % by weight.

EXAMPLES

Manufacturing Example 1: Production of an Antibody Specifically Reacting with Free AIM 1. Production of Mouse Anti-Human AIM Monoclonal Antibody An antibody No. 1 and an antibody No. 2 were mouse anti-human AIM monoclonal antibodies and were obtained by the following procedure.

Emulsion was produced by mixing full-length human rAIM (1 mg/ml) as an antigen with an equal amount of TiterMax Gold (G-1 Funakoshi). Two 8-week-old female Balb/c mice (Charles River Laboratories) were used as immunized animals, and 100 μL of an antigen solution was administered to the sole of the hind foot. The same administration was performed 2 weeks later, and after another 2 weeks or more, 100 μg of the antigen solution was administered to the sole of the hind foot to prepare for cell fusion performed 3 days later. Mouse P3U1 was used for myeloma cells.

Popliteal lymph nodes were aseptically removed from the mice after cardiac blood was collected under anesthesia and were placed on a beaker with #200 mesh and pressed with a silicon rod to prepare a cell suspension. The cells were centrifugally washed twice in RPMI 1640 and then the number of cells was counted. Myeloma cells in the logarithmic growth phase were collected by centrifugation, washed, and then adjusted so that the ratio of lymphocytes to myeloma cells was 5:1, and mixing centrifugation was performed. Cell fusion was performed by using PEG1500 (783641 Roche). Specifically, after a cell pellet was reacted with 1 mL of PEG solution for 3 minutes, then diluted in stages, and washed by centrifugation, a medium was added, and 200 μL was placed in each of 15 96-well plates for 1 week of culture. For the medium, a HAT supplement (21060-017 GIBCO) was added to a medium for myeloma cells to adjust the FBS concentration to 15%.

After the cryopreserved cells were thawed and proliferation culture was performed, $1 \times 10^8$ cells were administered to the abdominal cavity of a nude mouse (BALB/cAJcl-nu/nu Nippon Claire) to which 0.5 ml of pristane (42-002 Cosmo Bio) was intraperitoneally administered 1 week or more before, and after about 2 weeks, 4 to 12 ml of ascites was obtained. After removing a solid matter by centrifugation, the ascites was cryopreserved. Subsequently, antibodies were purified from the cryopreserved ascites to obtain an antibody No. 1 and an antibody No. 2.

Example 1: Confirmation of Effect of Preventing Non-Specific Reaction by Adding Anti-Human IgM Antibody 1. Separation of Human Specimen by Column Chromatography Size fractionation of 10 μL of a human specimen was performed by size exclusion chromatography (TSKgel G3000 SWXL, Tosoh) to obtain respective fractions of complex AIM and free AIM (complex AIM: fraction Nos. 6 and 7, free AIM: fraction Nos. 14 and 15). HPLC was performed by using a phosphate buffer at a flow rate of 1 mL/min to acquire 500 μL of each fraction.

2. Production of Antibody No. 2-Bound Magnetic Beads

1) The absorbance of the antibody No. 2 dialyzed with 150 mM potassium phosphate buffer (pH 7.8) was measured and adjusted to Abs 0.5 by using the same buffer solution.
2) With the buffer solution, 1 mL (30 mg/mL) of Dynabeads M-450 Epoxy manufactured by Dynamic Biotech was washed 3 times, and 1 mL of the antibody solution of 1) was added. Rotary stirring was performed at 25° C. for 18 hours or more.
3) The beads prepared at 2) were washed twice with a bead blocking buffer [50 mM Tris, 150 mM NaCl, 0.1% BSA, 0.09% $NaN_3$, pH 7.8]. The antibody remaining in the solution and not bound to the beads was removed by removing the buffer solution by washing. Subsequently, 1 mL of the bead blocking buffer was added and stirred, and rotary stirring was performed at 25° C. for 18 hours or more.
4) After washing the beads twice with the bead blocking buffer, 1 mL of the bead blocking buffer was added and stirred. These were used as antibody-bound magnetic beads and stored at 4° C. until use.

3. Production of Ruthenium-Labeled Antibody No. 1

1) To 312.5 μL of an antibody No. 1 solution dialyzed with 150 mM potassium phosphate buffer (pH 7.8), 14.1 μL of 10 mg/mL ruthenium complex (Origin Tag-NHS ESTER manufactured by IGEN) was added, and the solution was stirred for 30 minutes. Subsequently, 50 μL of 2M glycine was added, and the solution was stirred for 20 minutes.
2) A ruthenium complex-labeled antibody was applied to gel filtration column chromatography (Sephadex G-25 manufactured by GE Healthcare Bioscience) packed in a glass tube with a diameter of 1 cm and a height of 30 cm to isolate and purify the non-labeling ruthenium complex and the ruthenium complex-labeled antibody. Elution was performed with 10 mM potassium phosphate buffer (pH 6.0).

4. Confirmation of Effect of Preventing Non-Specific Reaction by Adding Anti-Human IgM Antibody 1) From each of the complex AIM fractions (No. 6 and 7), 10 μL was taken to add a total of 20 μL to 200 μL of a reaction solution [50 mM HEPES, 50 mM NaCl, 0.05% Tween 20, 1 mM EDT-4Na, 0.5% BSA, 0.09% $NaCl_3$, 100 μg/mL Mouse IgG, pH 7.8] or an anti-IgM antibody-containing reaction solution. Similarly, 10 μL of each of the free AIM fractions (Nos. 14 and 15) was taken to add a total of 20 μL to 200 μL of the reaction solution or the anti-IgM antibody-containing reaction solution. For the anti-IgM antibody, HBR-1, HBR-3, HBR-6, HBR-9, HBR-20, HBR-21, HBR-23, or HBR-26 was all adjusted to 50 μg/mL based on the reaction solution and used. HBR-6 and HBR-20 are anti-IgM monoclonal antibodies.
2) To the solution, 25 μL of antibody No. 2-bound magnetic beads diluted to a concentration of 0.5 mg/mL with a bead diluent [50 mM HEPES, 100 mM NaCl, 0.1% Tween 20, 1 mM EDT-4Na, 0.5% BSA, 0.09% $NaN_3$, pH 7.8] was added and reacted at 30° C. for 9 minutes (first reaction).

Subsequently, the magnetic beads were trapped with a magnet, the liquid in the reaction tube was extracted, and the magnetic beads were washed twice with 350 μL of washing liquid [50 mmol/L Tris HCl, 0.01% (W/V) Tween 20, 0.15 mol/L NaCl, pH 7.5] to remove non-specific binding substances other than the antigen-antibody reaction (BF separation).
3) Subsequently, 200 μL of a ruthenium-labeled antibody No. 1 diluted with a dilute solution for ruthenium [50 mM HEPES, 50 mM NaCl, 0.05% Tween 20, 1 mM EDT-4Na, 0.5% BSA, 0.09% $NaN_3$, 100 μg/mL mouse IgG, pH 7.8] to a concentration of 0.6 μg/mL was added and reacted at 30° C. for 9 minutes (second reaction).

The magnetic beads after the reaction were trapped with a magnet, the liquid in the reaction tube was extracted, and the magnetic beads were washed twice with 350 μL of the washing liquid to remove non-specific binding substances other than the antigen-antibody reaction (BF separation).
4) Subsequently, 300 μL of tripropylamine was placed in the reaction tube and mixed with the magnetic beads. By applying electrical energy in this state, the ruthenium complex emitted light, and the emission intensity was detected by a detector.

After the operation of adding the magnetic beads to the reaction tube, this was performed on an automatic ruthenium complex luminescence measuring machine, Picolumi III.

5. Results

The results are shown in FIG. 1. When a count ratio of F6+F7 was lower than a standard, the non-specific reaction of the antibody to complex AIM was probably more suppressed. When a count ratio of F14+F15 was lower than a standard, the sensitivity of the antibody to free AIM was probably more reduced. In the measurement systems to which the anti-IgM antibody was added, the count ratio of F6+F7 was 94.3%, 88.3%, 87.6%, 92.3%, 81.8%, 91.2%, 91.3%, or 91.0% with respect to the measurement system to which the anti-IgM antibody was not added. Therefore, the non-specific reaction of the antibody to complex AIM was suppressed in any of the measurement systems to which the anti-IgM antibody was added.

Example 2: Confirmation of Effect of Preventing Non-Specific Reaction by Adding Anti-Human IgM Antibody in Measurement System of the Present Invention The effect of preventing a non-specific reaction by adding an anti-human IgM antibody in the measurement system of the present invention was verified by the following procedure using the ECL method.
1. Production of Antibody-Bound Magnetic Beads
   The procedure was the same as Example 1.
2. Production of Ruthenium-Labeled Antibody
   The procedure was the same as Example 1.
3. Measurement of Free AIM Amount and IgM-AIM Amount with Free AIM-Specific Antibody
1) A healthy person serum sample was separated into fractions by the same procedure as Example 1, and the fraction containing IgM-AIM and the fraction containing free AIM were diluted to 1/10 with a reaction solution [50 mM HEPES, 50 mM NaCl, 0.05% Tween 20, 1 mM EDT-4Na, 0.5% BSA, 0.09% $NaN_3$, 100 µg/mL mouse IgG, 50 µg/mL anti-human IgM antibody, pH 7.8] to produce a specimen diluted solution. Subsequently, 100 µL of the reaction solution was placed in the reaction tube, and 2 µL of the specimen diluted solution was added.
2) To the solution, 25 µL of antibody No. 2-bound magnetic beads diluted to a concentration of 0.5 mg/mL with a bead diluent [50 mM HEPES, 100 mM NaCl, 0.1% Tween 20, 1 mM EDT-4Na, 0.5% BSA, 0.09% $NaN_3$, pH 7.8] was added and reacted at 30° C. for 9 minutes (first reaction).

Subsequently, the magnetic beads were trapped with a magnet, the liquid in the reaction tube was extracted, and the magnetic beads were washed twice with 350 µL of washing liquid [50 mmol/L Tris HCl, 0.01% (W/V) Tween 20, 0.15 mol/L NaCl, pH 7.5] to remove non-specific binding substances other than the antigen-antibody reaction (BF separation).
3) Subsequently, 200 µL of a ruthenium-labeled antibody No. 1 diluted with a dilute solution for ruthenium [50 mM HEPES, 50 mM NaCl, 0.05% Tween 20, 1 mM EDT-4Na, 0.5% BSA, 0.09% $NaN_3$, 100 µg/mL mouse IgG, pH 7.8] to a concentration of 0.6 µg/mL was added and reacted at 30° C. for 9 minutes (second reaction).

The magnetic beads after the reaction were trapped with a magnet, the liquid in the reaction tube was extracted, and the magnetic beads were washed twice with 350 µL of the washing liquid to remove non-specific binding substances other than the antigen-antibody reaction (BF separation).
4) Subsequently, 300 µL of tripropylamine was placed in the reaction tube and mixed with the magnetic beads. By applying electrical energy in this state, the ruthenium complex emitted light, and the emission intensity was detected by a detector.

After the operation of adding the magnetic beads to the reaction tube, this was performed on an automatic ruthenium complex luminescence measuring machine, Picolumi III.
5) For a specimen diluted solution produced by diluting the healthy person serum sample with a reaction solution containing no anti-human IgM antibody to 1/10, the operations 1) to 4) were repeated to obtain a control.

FIG. 2 shows a percentage of an IgM-AIM detection amount or a percentage of a free AIM detection amount to a total amount of the IgM-AIM detection amount and the free AIM detection amount. The measurement system of Example 2 is a measurement system using the antibody No. 2, which is a monoclonal antibody specific for free AIM, and therefore, when the percentage of the IgM-AIM amount to the total of the IgM-AIM amount and the free AIM amount, the non-specific reactions due to IgM-AIM are probably decreased. Therefore, the detected amount of IgM-AIM probably represents a degree of the non-specific reaction due to IgM-AIM to the antibody No. 2.

In the measurement system to which the anti-human IgM antibody was added, the IgM-AIM amount was 2.4% of the total amount of the IgM-AIM amount and the free AIM amount, and in the measurement system to which the anti-human IgM antibody was not added, the IgM-AIM amount was 7.5% of the total amount of the IgM-AIM amount and the free AIM amount. Therefore, it was found that the addition of an anti-human IgM antibody can suppress the non-specific reaction of the antibody specifically binding to free AIM due to IgM-AIM.

Figure 3:
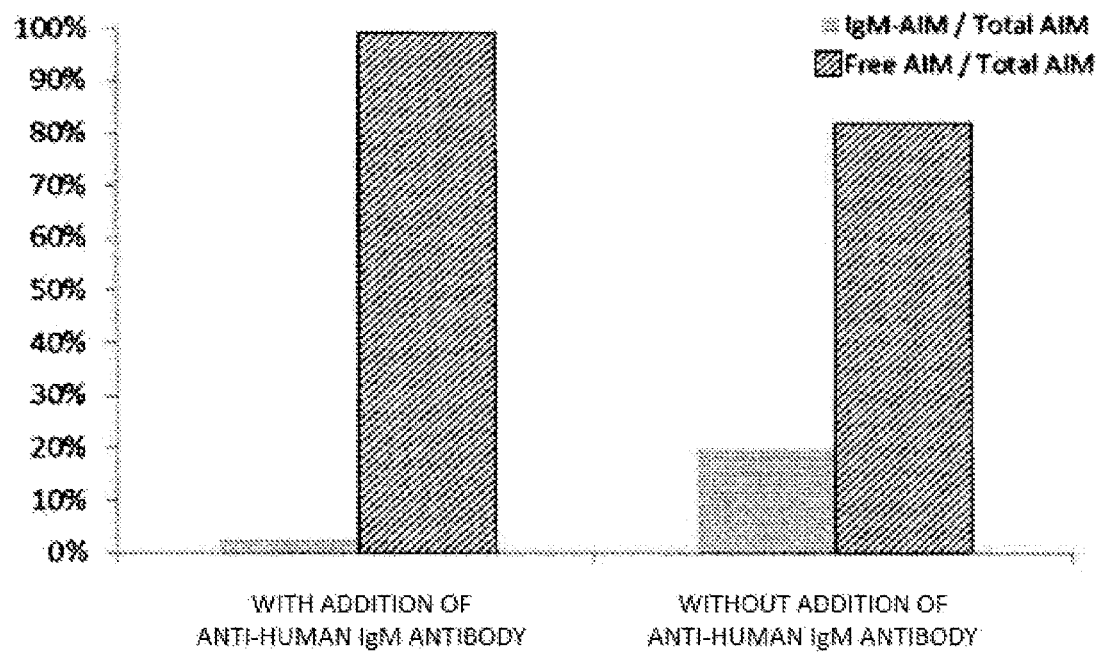
FIG. 3 is a graph showing a comparison between an embodiment of an immunoassay method of the present invention and an existing measurement system.

Example 3: Comparison Between Measurement System of the Present Invention and Existing Measurement System The degree of the non-specific reaction due to the IgM-AIM amount was compared between the measurement system of the present invention and an existing measurement system.
(3-1) Measurement System of the Present Invention
By using the same procedure as the ECL method of Example 2, the free AIM amount and the IgM-AIM amount were measured for each of the fractions containing IgM-AIM and containing free AIM.
(3-2) Existing Measurement System
By using a Human AIM ELISA kit (CY-8080, CircuLex), the free AIM amount and the IgM-AIM amount were measured for each of the fractions containing IgM-AIM and containing free AIM. The protocol followed the package insert of the Human AIM ELISA kit. The results are shown in FIG. 3.

In the measurement system of the present invention, the IgM-AIM amount was 2.5% of the total amount of the IgM-AIM amount and the free AIM amount, and in the existing measurement system, the IgM-AIM amount was 19.7% of the total amount of the IgM-AIM amount and the free AIM amount. Therefore, it was demonstrated that the measurement system of the present invention has significantly less non-specific reactions than the existing measurement system.

Example 4: Detection of NASH by the Measurement System of the Present Invention or the Existing Measurement System (4-1) Measurement System of the Present Invention
By using the same procedure as the ECL method of Example 2, the free AIM amount was measured in 42 specimens of NAFL patient sera, 141 specimens of NASH patient sera, and 26 specimens of NASH-HCC patient sera to study whether a significant difference was generated among the patients.

(4-2) Existing Measurement System

Figure 4:
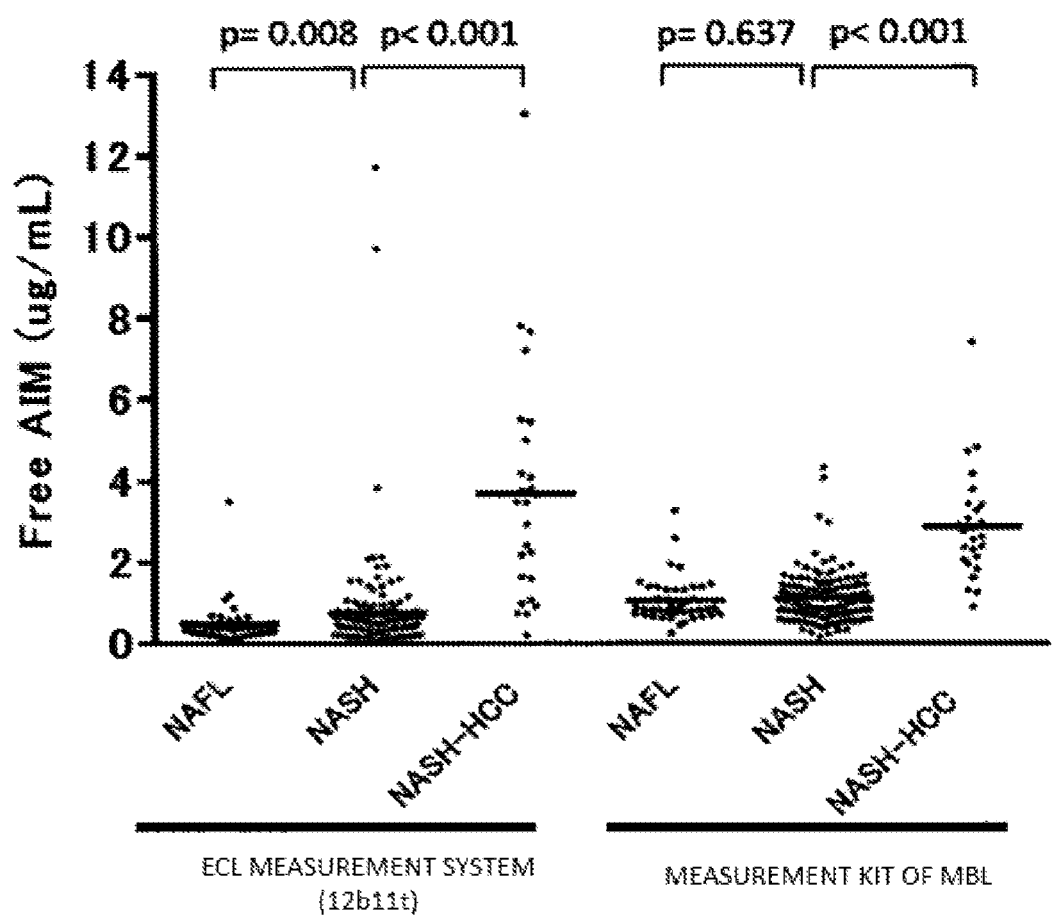
FIG. 4 is a graph showing a comparison between an embodiment of an immunoassay method of the present invention and an existing measurement system in detection of NASH.

By using the Human AIM ELISA kit (CY-8080, CircuLex), the free AIM amount was measured in 42 specimens of NAFL patient sera, 141 specimens of NASH patient sera, and 26 specimens of NASH-HCC patient sera to study whether a significant difference was generated among the patients. The protocol followed the package insert of the Human AIM ELISA kit. The results are shown in FIG. 4.

In the measurement system of the present invention, the free AIM amount in the NASH patient sera was significantly higher than the free AIM amount in the NAFL patient sera. In the existing measurement system, the free AIM amount in the NASH patient sera was at the same level as the free AIM amount in the NAFL patient sera, and no significant difference was observed between the patients. In the measurement system of the present invention, the addition of the anti-IgM antibody to the measurement system can probably suppress the non-specific reaction of IgM-AIM to the free AIM-specific antibody so that a significant difference is generated between the free AIM amount in the NASH patient sera and the free AIM amount in the NAFL patient sera.

INDUSTRIAL APPLICABILITY

According to the present invention, in the immunoassay method of a biological sample containing complex AIM and free AIM, the specificity for free AIM of an antibody specifically reacting with free AIM can further be improved. According to the present invention, NASH can be diagnosed without imposing a burden on patients and medical staffs.

The invention claimed is:

1. An immunoassay method for free apoptosis inhibitor of macrophage (AIM) in a biological sample containing complex AIM and free AIM, the method comprising:

bringing the biological sample into contact with an antibody specifically reacting with free AIM or a fragment thereof having antigen-antibody reaction activity with free AIM in a presence of an added anti-IgM antibody or a fragment thereof having an antigen-antibody reaction activity with IgM, wherein the added anti-IgM antibody or fragment thereof is present in an amount that suppresses non-specific reactions of the antibody specifically reacting with free AIM.

2. The immunoassay method for free AIM in a biological sample according to claim 1, wherein the biological sample is a body fluid sample.

3. The immunoassay method for free AIM in a biological sample according to claim 1, wherein the antibody specifically reacting with free AIM is a monoclonal antibody.

4. The immunoassay method for free AIM in a biological sample according to claim 1, wherein the added anti-IgM antibody is an anti-human IgM antibody.

5. The immunoassay method for free AIM in a biological sample according to claim 1, wherein the added anti-IgM antibody is an anti-human IgM monoclonal antibody.

6. The immunoassay method for free AIM in a biological sample according to claim 5, wherein a binding affinity of the added anti-human IgM monoclonal antibody to IgM is a Kd of at least about 10-4 M.

7. The immunoassay method for free AIM in a biological sample according to claim 1, wherein the antibody specifically reacting with free AIM binds to an epitope within a SRCR2 domain of human AIM and does not bind to a SRCR1 domain.

8. The immunoassay method for free AIM in a biological sample according to claim 1, wherein the antibody specifically reacting with free AIM preferably binds to an epitope within a SRCR2 domain of human AIM and does not bind to either a SRCR1 domain or a SRCR3 domain.

* * * * *